United States Patent [19]

Nawracala et al.

[11] Patent Number: 6,018,388
[45] Date of Patent: Jan. 25, 2000

[54] MICROTITER PLATE

[76] Inventors: Bernd Nawracala, Baumgarten 16, D-76199 Karlsruhe; Manfred Berndt, Hellenstr. 55, D-76337 Waldbronn; Guenter Gauglitz, Panoramastr. 54, D-72070 Tuebingen; Gunther Elender, Obersimbach 66, D-94081 Fuerstenzell; Dieter Graefe, Hanns-Eisler-Str. 32, D-07745 Jena; Guenter Berthel, Freiligrathstr. 24, D-07743 Jena, all of Germany

[21] Appl. No.: 09/252,311

[22] Filed: Feb. 18, 1999

[30] Foreign Application Priority Data

Feb. 18, 1998 [DE] Germany .................... 198 06 681

[51] Int. Cl.⁷ .................................................. G01N 21/03
[52] U.S. Cl. .................... 356/246; 356/440; 422/104; 435/288.4
[58] Field of Search .................................. 356/246, 244, 356/440; 422/101, 102, 104, 942; 435/288.4, 305.2, 809; 436/165, 177, 809; 250/576

[56] References Cited

U.S. PATENT DOCUMENTS

| | | |
|---|---|---|
| 4,319,841 | 3/1982 | Suovaniemi et al. .................... 356/246 |
| 4,659,222 | 4/1987 | Ekholm .................................... 356/246 |
| 4,682,891 | 7/1987 | De Macario et al. .................... 356/246 |
| 5,084,246 | 1/1992 | Lyman et al. ............................ 356/246 |
| 5,110,556 | 5/1992 | Lyman et al. ............................ 356/246 |
| 5,319,436 | 6/1994 | Manns et al. ............................ 356/246 |
| 5,457,527 | 10/1995 | Manns et al. ............................ 356/246 |
| 5,487,872 | 1/1996 | Hafeman et al. ........................ 356/246 |
| 5,888,454 | 3/1999 | Leistner et al. ......................... 356/246 |

*Primary Examiner*—Hoa Q. Pham
*Attorney, Agent, or Firm*—McAulay Nissen Goldberg Kiel & Hand, LLP

[57] ABSTRACT

A microtiter plate is formed of a bottom plate which is transparent for light and a cavity plate which is open at two surfaces facing one another and which has a matrix-shaped arrangement of cavities or wells. The bottom plate and cavity plate are fixedly connected with one another in a liquid-tight manner. The bottom plate has a thickness of from 0.01 mm to approximately 5 mm and has planar surfaces without structures. It has, at its first surface facing the wells, a layer system formed of at least two layers with different indexes of refraction. The bottom plate is provided at its second surface remote of the wells with a coating which sharply reduces the reflectivity of this surface. The bottom plate is recessed into the lower part of the cavity plate in such a way that it does not project over a support surface located in the cavity plate.

9 Claims, 2 Drawing Sheets

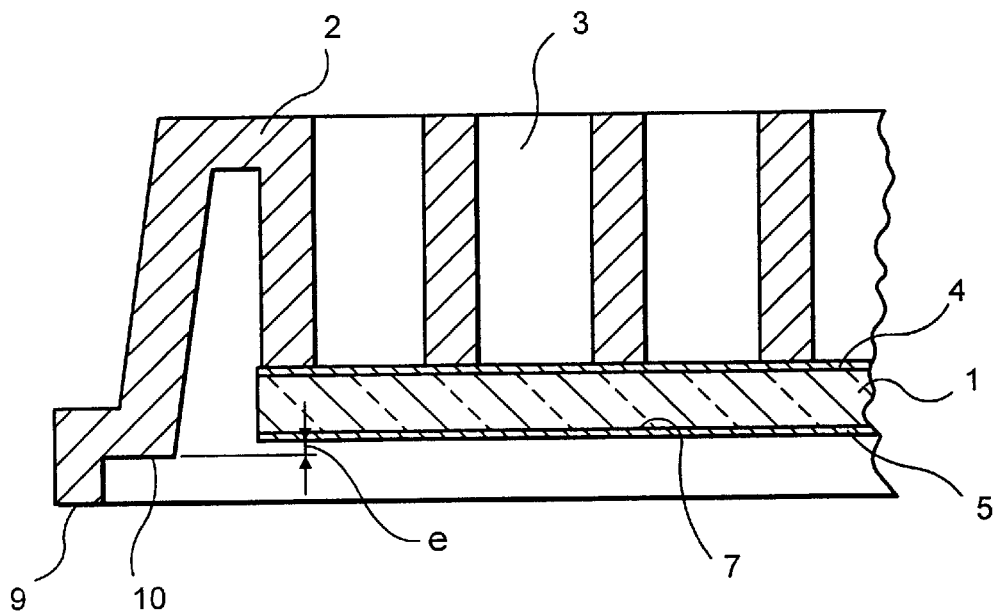
F I G. 3
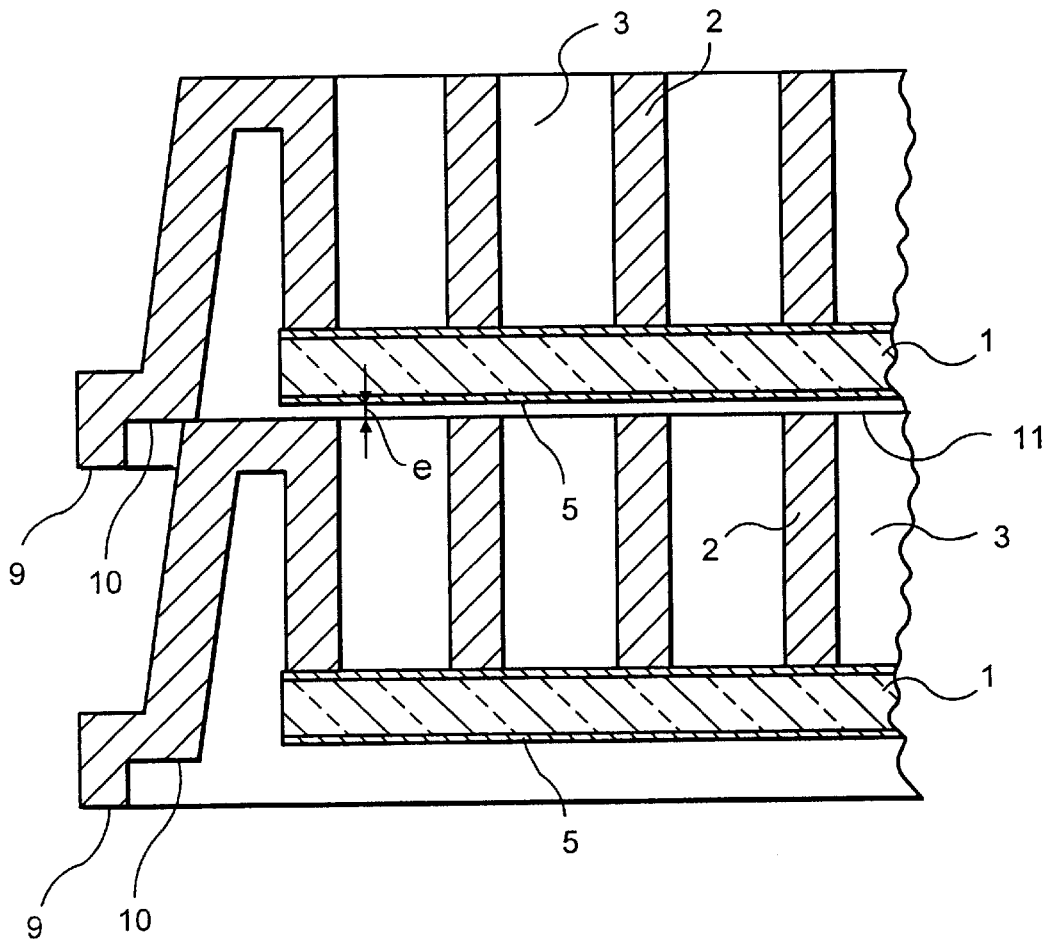
F I G. 4

MICROTITER PLATE

BACKGROUND OF THE INVENTION a) Field of the Invention

The invention is directed to a microtiter plate for screening processes using the method of reflectometric interference spectroscopy (RIS) for receiving a plurality of samples which are examined simultaneously or one after the other to detect physical, chemical, biological or biochemical reactions and interactions.

b) Description of the Related Art

A process and a device for carrying out testing of physical, chemical, biological or biochemical reactions and interactions using the method of reflectometric interference spectroscopy (RIS) are described in DE 196 15 366 A1. In this case, a plurality of samples which are arranged areally or in matrix form on a substrate plate are irradiated by light of different wavelengths from a tunable light source or scanning monochromator which is arranged following a polychromatic light source. Accordingly, the imaging of the radiation component reflected at a boundary surface of every sample is carried out by imaging elements arranged downstream on a spatially resolving detector array or a video camera. This enables wavelength-selective detection of the radiation intensities or intensities of the imaged interference which are influenced by the samples and also makes it possible to determine a wavelength-dependent interference spectrum associated with each of the samples and the derivation of parameters characterizing the reactions and interactions to be examined.

Microtiter plates, as they are called, are used for examination of the physical, chemical or biological characteristics of a quantity of samples in parallel. The samples to be examined are arranged in matrix form in small cavities or wells.

Microtiter plates of the type mentioned above are known, for example, from U.S. Pat. No. 5,457,527, WO 97/22754 and WO 95/03538. They comprise a specimen plate, or cavity plate, and a bottom plate, wherein the bottom plate is made of plastic or glass. The bottom plate and cavity plate are joined together in such a way that the bottom plate closes the wells of the cavity plate at the bottom. The bottom plate can be transparent. The bottom plate can be constructed in a special manner for special detection methods. For example, WO 95/22754 and WO 95/03538 describe microtiter plates which have a prism structure or lens structure or a grating structure at the location of each well. In both cases, the bottom plate is provided with coatings which are suitable for surface plasmon resonance (SPR) or form a waveguide channel for the light. These microtiter plates are accordingly configured for special applications of optical detection such as plasmon resonance methods or resonant mirror methods. Such elaborate microtiter plates with structures on the bottom plate are not required for use with RIS methods.

It is known from U.S. Pat. No. 5,319,436 and U.S. Pat. No. 5,457,527 to connect the bottom plate and the cavity plate through the action of heat, wherein the two plates are made of plastic, the bottom plate is transparent and the cavity plate is opaque.

As is known from DE 196 15 366 A1, the RIS process requires the arrangement of a determined transducer surface having a suitable RIS layer system. If this measurement process is to be carried out in a parallel manner, a matrix-shaped arrangement of the samples arranged in the wells is suitable for this purpose. A matrix arrangement corresponding to the standard grids of microtiter plates is recommended for favorable automatic handling of the liquid samples or samples dissolved in liquid.

OBJECT AND SUMMARY OF THE INVENTION

It is the primary object of the invention to provide a microtiter plate for analyses by the RIS method which is constructed in a simple manner and enables highly accurate measurements and analyses of samples.

According to the invention, this object is met by a microtiter plate for additive screening processes, comprising a bottom plate made of a material which is transparent for light and a cavity plate which is open at two surfaces facing one another and which has a matrix-shaped arrangement of cavities or wells. The bottom plate and cavity plate are fixedly connected with one another in a liquid-tight manner. The bottom plate is provided with at least one optically active layer at its surface facing the wells. The bottom plate has a thickness of from 0.1 mm to approximately 5 mm and has planar surfaces without structures. At its first surface facing the wells, a layer system is formed of at least two layers with different indexes of refraction. The bottom plate is provided at its second surface remote of the wells with a coating which sharply reduces the reflectivity of this surface.

The microtiter plate for the RIS screening process has a bottom plate which has no structures and is defined by planar surfaces. A RIS layer system is arranged on the upper surface of the bottom plate as a transducer surface. This layer system can cover the entire upper surface of the bottom plate, but can also be arranged only in the regions of the wells. This layer system does not form a waveguide channel. The bottom plate is constructed in such a way that the light irradiated in from the bottom from a suitable light source, such as that described in DE 196 15 366 A1, can penetrate without hindrance and is reflected in a superimposed manner suitable for interference at the layer system which is applied to the upper surface of the bottom plate and whose spectral reflection behavior is influenced by the applied samples. The bottom surface of the bottom plate facing the light source is provided with a reflection-reducing coating which causes a reflectivity of less than 10% in the given wavelength range and at the given angle of incidence and polarization of the RIS measuring device which is used, so that an effective suppression of troublesome reflections at the underside of the microtiter plate is achieved. In order to achieve optimum ratios for the RIS process, a wavelength range of approximately 400 nm to 800 nm, an angle of incidence of about 50° and an s-position (vertical to the incident angle of the radiated light) are advisably provided.

As is described in DE 196 15 366, a special RIS coating is required on the glass substrate for the RIS process. Together with the substrate and a sensitive layer arranged over the layer system, this layer system, which comprises a layer with a high refractive index and a layer with a lower refractive index compared to the first layer, forms a system capable of interference whose wavelength-dependent reflection behavior and interference behavior is detected and which supplies information about the layer thickness and index of refraction of the sensitive layer.

When applying the RIS process, it is advantageous when the layer system comprises a high refractive index layer with a thickness of 5 nm to 1000 nm and a low refractive index layer with a thickness of 5 nm to 1000 nm which is arranged on top of the latter, wherein this layer system is arranged on the surface of the bottom plate facing the wells.

The layer system can also be constructed so as to have a low refractive index layer with a thickness of 5 nm to 1000 nm and a high refractive index layer with a thickness of 5 nm to 1000 nm arranged on top of the latter, wherein the layer system is arranged on the surface of the bottom plate facing the wells.

It is important that a boundary transition with a high jump in the index of refraction between these layers supplies a high reflectance factor which, together with the reflection at the additive boundary layer originating from the sample, supplies a characteristic interference signal.

For optimum functioning of the microtiter plate for the RIS process in the visible wavelength range, it is advantageous when the bottom layer with a high refractive index has a thickness of 5 nm to 50 nm and is made of $TiO_2$ or $Ta_2O_5$ and the low refractive index layer which is arranged above the latter and faces the wells has a thickness of 200 nm to 600 nm and is made of $SiO_2$.

The microtiter plate is easy to manufacture with respect to manufacturing technique when the bottom plate and cavity plate are connected with one another by a material engagement. This can be carried out, for example, in that the cavity plate and the bottom plate are connected with one another by a glue or cement and in that the glue layer or cement layer has a thickness such that unevenness at the surfaces that are glued or cemented together is compensated.

In order to bind the materials to be tested, a hydrogel, known per se, is applied to the outer layer of the first surface of the bottom plate by chemical covalent bonding or by adsorption and the hydrogel is functionalized in a manner known per se by biological and/or synthetic molecules. As is known per se, this hydrogel is, e.g., a polysugar such as dextran, agarose or starch, or a synthetic polymer such as polyethylene glycol, polyvinyl alcohol, polyacrylamide or a derivative of these polymers.

The advantage of the solution according to the invention consists primarily in that it provides an easily manufactured microtiter plate which is necessary for parallelizing the RIS process. In this connection, it is especially advantageous that this microtiter plate comprises a glass bottom plate which is provided with planar surfaces without structures and which contains neither grating structures nor any other profiles or waveguide channels. This bottom plate has a layer system suitable for carrying out the RIS process on one side and an anti-reflection coating on the other side. The entire microtiter plate is so outfitted and dimensioned that its dimensions substantially conform to the standard dimensions of microtiter plates, so that automated handling of samples and liquid is made possible. These standard dimensions are indicated, for example, in the "Journal of Biomolecular Screening", Vol. 1, Number 4, 1996, pages 163 to 168.

In order to facilitate stacking of the microtiter plates and, at the same time, to protect the coating at the lower surface of the bottom plate against contamination and damage, the bottom plate is arranged so as to be recessed in the cavity plate in accordance with recommendations in the "Journal of Biomolecular Screening", so that when the microtiter plate is placed on a planar depositing surface or when the microtiter plates are stacked, the cavity plates or parts thereof are utilized as a standing surface or stacking surface (support surface). There remains below the bottom plate a sufficient distance or sufficient clearance relative to the planar depositing surface or stacking surface or support surface of the next microtiter plate.

The invention will be described more fully hereinafter with reference to an embodiment example.

DESCRIPTION OF THE DRAWINGS

In the drawings:

FIG. 3 is an enlarged view of a section through a portion of a microtiter plate comprising bottom plate and cavity plate; and FIG. 4 shows two stacked microtiter plates.

DESCRIPTION OF THE PREFERRED EMBODIMENTS

Figure 1A:
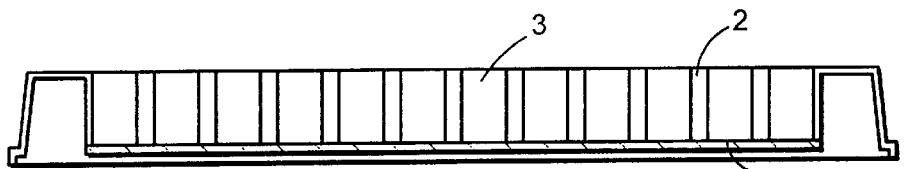
FIG. 1a is a simplified view showing a section through a microtiter plate.
Figure 1B:
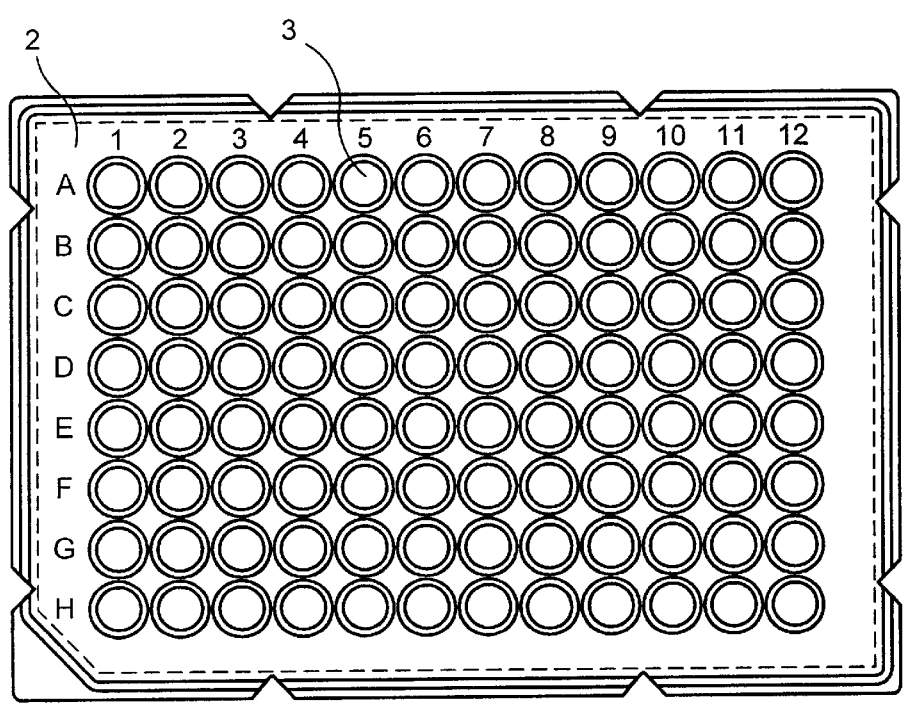
FIG. 1b is a top view of the cavity plate of a microtiter plate.
Figure 1C:
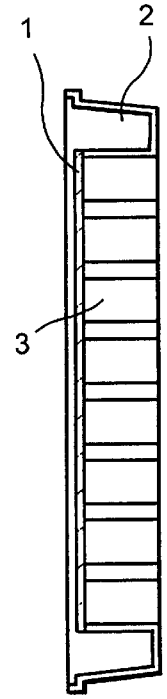
FIG. 1c is a simplified view showing a section through the narrow surface of a microtiter plate.

The microtiter plate shown in different sections and in a top view in FIGS. 1a, 1b and 1c comprises a planar, unstructured bottom plate 1 and a cavity plate 2 having continuous cavities or wells 3 arranged in matrix form. The bottom plate 1 and cavity plate 2 are connected with one another in a liquid-tight manner through the agency of a material, for example, by means of cement or glue or by adhesion with sealing, so that the wells 3 form small receptacles in which the samples to be examined are inserted.

Figure 2:
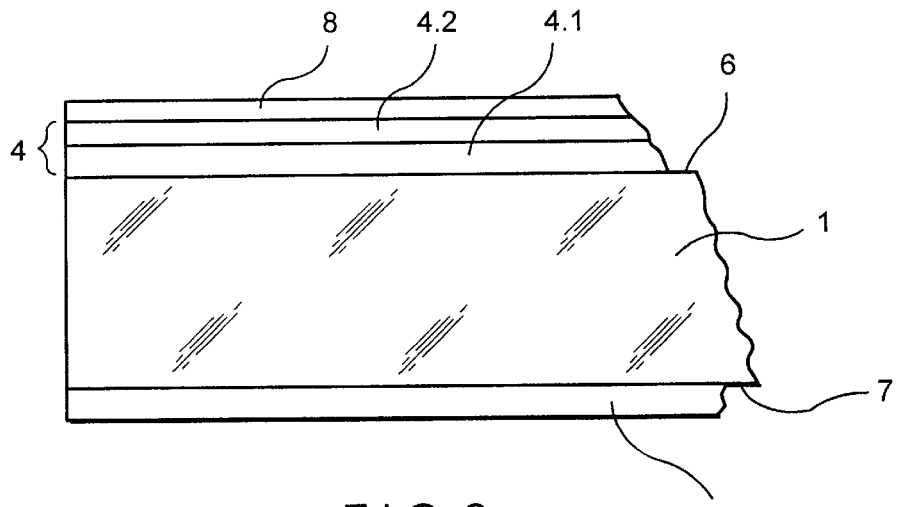
FIG. 2 shows a section through the bottom plate with layers arranged thereon.

As can be seen from FIG. 2, the bottom plate 1 is provided on its side facing the wells 3 with a layer system 4 formed of at least two layers. This layer system 4 has a plurality of layers 4.1 and 4.2 with different indexes of refraction on the surface 6 of the bottom plate 1 contacting the cavity plate 2. Accordingly, the layer 4.1 arranged directly on the surface 6 can have a higher index of refraction than the layer 4.2 arranged above it. The reverse case is also possible, so that the layer 4.1 arranged on the surface 6 has a lower index of refraction than the layer 4.2 lying on top of it. The bottom plate 1 itself has a thickness of about 0.01 mm to about 5 mm and is made of a material which is transparent to light, e.g., a plastic or glass.

The thickness of the layers 4.1 and 4.2 on the surface 6 is approximately 5 nm to 1000 nm. According to a preferred embodiment example, especially for the application of the RIS process in the visible wavelength range, the layer 4.1 is a high refractive index layer with a thickness between 5 nm and 50 nm. Ideally, this layer is made from $TiO_2$ or $Ta_2O_5$. In this preferred embodiment form, the layer 4.2 arranged on top of the latter is the layer with a low refractive index. It is made of $SiO_2$ and has a thickness of between 200 nm and 600 nm.

In order that light loss and disturbing reflections for the light radiated at the surface 7 located opposite to the surface 6 and superpositions on the reflected radiation components originating from the upper layer system 4 can be kept as low as possible, a reflection-reducing layer 5 is applied to this surface 7. This reflection-reducing layer 5 brings about a 10-% reduction in the light loss caused by reflection in the given wavelength range and at the given angle of incidence and s-polarization. According to an advantageous arrangement, the reflection-reducing layer reduces the light loss caused by reflection in the wavelength range of approximately 400 nm to approximately 800 nm at a light incidence angle of approximately 50° and with s-polarization to less than 10%.

When a glue layer or cement layer is used, it is advantageous in technical respects relating to manufacturing when the cement layer or glue layer (not shown in the drawings)

used for connecting the bottom plate 1 and cavity plate 2 has a thickness such that unevenness in the surfaces of the bottom plate 1 and cavity plate 2 to be joined is extensively compensated.

The layers 4.1 and 4.2 can cover the entire surface 6, but may also be provided only in the location of the wells 3 and, in this way, form the bottom surface of the wells 3. A known hydrogel 8 is applied to the layer 4.2 as a sensitive layer. The wells 3 are arranged in the cavity plate 2 in matrix form in determined grids, e.g., with a grid pattern of 8×12, 16×24, 24×36, 32×48, 48×72, 64×96, etc. The size of the microtiter plate is adapted to the usual automation arrangements for handling the samples and to the corresponding pipetting devices and analytic and measurement equipment.

FIG. 3 shows an enlarged section through the microtiter plate according to FIG. 1a, wherein it is shown that the bottom plate 1 does not project over the lower edge 9 of the cavity plate 2. A shoulder with a support surface 10 is provided in the lower area of the cavity plate 2, wherein there is a distance e between the lower surface 7 with layer 5 of the bottom plate 1 and this support surface 10.

FIG. 4 shows a schematic view of the ratios in two microtiter plates which are stacked one on top of the other. As a result of the arrangement of the microtiter plate shown in an enlarged view in FIG. 3, when a plurality of microtiter plates are stacked and when the support surface 10 of the upper plate rests on the upper surface 11 of the lower plate, damage to the underside of the bottom plate 1 with its reflection-reducing layer 5 is reliably prevented. It is clear from this view that there is a sufficiently great distance e between the bottom plate 1 of the upper microtiter plate and the upper surface 11 of the bottom microtiter plate in order to reliably prevent contact and any possible damage to the bottom plate 1 with its reflection-reducing layer 7.

While the foregoing description and drawings represent the preferred embodiments of the present invention, it will be obvious to those skilled in the art that various changes and modifications may be made therein without departing from the true spirit and scope of the present invention.

What is claimed is:

1. A microtiter plate for additive screening processes, comprising:
   a bottom plate made of a material which is transparent for light and a cavity plate which is open at two surfaces facing one another and which has a matrix-shaped arrangement of cavities or wells;
   said bottom plate and cavity plate being fixedly connected with one another in a liquid-tight manner; and wherein the bottom plate is provided with at least one optically active layer at its surface facing the wells;
   said bottom plate having a thickness of from 0.01 mm to approximately 5 mm and having planar surfaces without structures;
   at its first surface facing the wells, a layer system being formed of at least two layers with different indexes of refraction; and
   said bottom plate being provided at its second surface remote of the wells with a coating which sharply reduces the reflectivity of this surface.

2. The microtiter plate according to claim 1, wherein the layer system comprises a high refractive index layer with a thickness of 5 nm to 1000 nm and a low refractive index layer with a thickness of 5 nm to 1000 nm which is arranged on top of the latter and wherein the high refractive index layer is arranged on the first surface of the bottom plate facing the wells.

3. The microtiter plate according to claim 1, wherein the layer system comprises a low refractive index layer with a thickness of 5 nm to 1000 nm and a high refractive index layer with a thickness of 5 nm to 1000 nm arranged on top of the latter and wherein the low refractive index layer is arranged on the first surface of the bottom plate facing the wells.

4. The microtiter plate according to claim 1, wherein the high refractive index layer has a thickness of 5 nm to 50 nm and is made of a compound selected from the group of $TiO_2$ or $Ta_2O_5$, and the low refractive index layer has a thickness of 200 nm to 600 nm and is made of $SiO_2$.

5. The microtiter plate according to claim 1, wherein the second surface remote of the wells is coated with an anti-reflection layer which has a reflectivity of less than 10% in a wavelength range of 400 nm to 800 nm at a light incidence angle of approximately 50° and with s-polarization of the incident light.

6. The microtiter plate according to claim 1, wherein the cavity plate and the bottom plate are connected with one another through the agency of a substance.

7. The microtiter plate according to claim 1, wherein the cavity plate and the bottom plate are connected with one another by a glue or cement, and wherein the glue layer or cement layer has a thickness such that unevenness at the surfaces that are glued or cemented together is compensated.

8. The microtiter plate according to claim 1, wherein a hydrogel, known per se, is applied to the outer layer of the first surface of the bottom plate by chemical covalent bonding or by adsorption, and wherein the hydrogel is functionalized, as is known per se, by biological and/or synthetic molecules.

9. The microtiter plate according to claim 1, wherein the hydrogel is a polysugar selected from a group consisting of dextran, agarose ands starch, or a synthetic polymer selecting from a group consisting of polyethylene glycol, polyvinyl alcohol, polyacrylamide and a derivative of these polymers.

* * * * *